United States Patent
Plaβky et al.

(10) Patent No.: US 9,095,376 B2
(45) Date of Patent: Aug. 4, 2015

(54) DEVICE FOR FASTENING A MARKER DEVICE TO A BONE

(75) Inventors: Norman Plaβky, Erfurt (DE); Manuel Millahn, München (DE); Blaine Warkentine, Royersford, PA (US)

(73) Assignee: Brainlab AG, Feldkirchen (DE)

( * ) Notice: Subject to any disclaimer, the term of this patent is extended or adjusted under 35 U.S.C. 154(b) by 972 days.

(21) Appl. No.: 12/554,107

(22) Filed: Sep. 4, 2009

(65) Prior Publication Data

US 2010/0063511 A1    Mar. 11, 2010

Related U.S. Application Data

(60) Provisional application No. 61/116,774, filed on Nov. 21, 2008.

(30) Foreign Application Priority Data

Sep. 5, 2008    (EP) .................................... 08163759

(51) Int. Cl.
*A61B 19/00* (2006.01)

(52) U.S. Cl.
CPC ............ *A61B 19/54* (2013.01); *A61B 19/5244* (2013.01); *A61B 2019/5416* (2013.01); *A61B 2019/5483* (2013.01); *A61B 2019/5487* (2013.01); *A61B 2019/5491* (2013.01)

(58) Field of Classification Search
CPC ........... A61B 19/54; A61B 2019/5416; A61B 2019/5487; A61B 19/5491
USPC .................... 606/96, 130; 600/424
See application file for complete search history.

(56) References Cited

U.S. PATENT DOCUMENTS

| | | | |
|---|---|---|---|
| 4,341,206 A * | 7/1982 | Perrett et al. .................... | 606/80 |
| 4,669,469 A | 6/1987 | Gifford, III et al. | |
| 4,947,502 A | 8/1990 | Engelhardt | |
| 5,100,424 A | 3/1992 | Jang et al. | |
| 5,575,794 A * | 11/1996 | Walus et al. .................. | 606/116 |
| 6,203,543 B1 | 3/2001 | Glossop | |
| 6,856,828 B2 * | 2/2005 | Cossette et al. ............... | 600/429 |
| 6,887,247 B1 * | 5/2005 | Couture et al. ................. | 606/96 |
| 7,840,253 B2 * | 11/2010 | Tremblay et al. ............. | 600/424 |
| 7,862,570 B2 * | 1/2011 | Russell et al. .................. | 606/87 |
| 8,147,496 B2 * | 4/2012 | Couture et al. ................. | 606/87 |
| 2002/0107518 A1 * | 8/2002 | Neubauer et al. ............... | 606/54 |
| 2003/0225329 A1 * | 12/2003 | Rossner et al. ............... | 600/424 |
| 2004/0068260 A1 | 4/2004 | Cossette et al. | |
| 2005/0070918 A1 | 3/2005 | Zwirnmann et al. | |
| 2005/0190380 A1 * | 9/2005 | Plassky et al. ................ | 356/614 |
| 2005/0238418 A1 * | 10/2005 | Surma et al. .................... | 403/24 |
| 2006/0069324 A1 * | 3/2006 | Block et al. .................... | 600/595 |

(Continued)

FOREIGN PATENT DOCUMENTS

| | | |
|---|---|---|
| DE | 201 03 416 | 7/2001 |
| EP | 1 561 431 | 8/2005 |
| EP | 1 588 672 | 10/2005 |

(Continued)

*Primary Examiner* — David Bates
(74) *Attorney, Agent, or Firm* — Tucker Ellis LLP

(57) ABSTRACT

A device for fastening a marker device to a bone, comprising a fixing element including a mounting for the marker device, comprising a spring designed to contact an abutment for exerting a force between the abutment and the fixing element in the direction of the bone.

13 Claims, 4 Drawing Sheets

(56) References Cited

U.S. PATENT DOCUMENTS

2007/0276403 A1* 11/2007 Franks et al. .................. 606/104
2009/0264737 A1* 10/2009 Haechler et al. .............. 600/424

FOREIGN PATENT DOCUMENTS

| WO | 95/13024 | 5/1995 |
| WO | 00/48508 | 8/2000 |

* cited by examiner

DEVICE FOR FASTENING A MARKER DEVICE TO A BONE

RELATED APPLICATION DATA

This application claims the priority of U.S. Provisional Application No. 61/116,774, filed on Nov. 21, 2008, which is hereby incorporated in its entirety by reference.

FIELD OF THE INVENTION

The present invention relates to a device for fastening a marker device to a bone, comprising a fixing element and a mounting for the marker device on the fixing element.

BACKGROUND OF THE INVENTION

In image-guided operations, it is necessary to provide objects such as bones or medical instruments with marker devices. A marker device consists for example of one or more reflective spheres which can be detected by sensors. The position of the marker device and therefore the position of the object can be determined from the position of the spheres with respect to each other.

One commercially available device for fastening a marker device to a bone consists of a screw, a clamping device, an adjusting screw and a sleeve which comprises a mounting for the marker device. When attaching the device, the screw is initially screwed into the bone, and the sleeve together with the adjusting screw and the clamping device is then fitted onto the screw. The clamping device is then fixed relative to the screw, and the sleeve is pressed against the bone in the desired alignment by means of the adjusting screw and thus fixed.

One of the disadvantages of this fastening device is that attaching it to the bone requires a large number of steps working on the patient and thus increases the length of time which the patient has to spend in the operating theatre.

SUMMARY OF THE INVENTION

It is the object of the present invention to provide a device for fastening a marker device to a bone which does not exhibit the disadvantages cited above.

This object is solved by a device for fastening a marker device to a bone, comprising a fixing element including a mounting for the marker device, and a spring designed to contact an abutment for exerting a force between the abutment and the fixing element in the direction of the bone. Advantageous embodiments may be gathered from the dependent patent claims.

A device for fastening a marker device to a bone comprises a fixing element including a mounting for the marker device, and a spring designed to contact an abutment for exerting a force between the abutment and the fixing element in the direction of the bone. The device is designed to be fixed to the bone by means of a screw. To this end, the device comprises a passage through which a screw can be guided and is guided when the device is being properly used. This passage preferably passes through the fixing element and the spring. The passage is preferably arranged centrally in the fixing element in order to minimize the torque exerted by the screw on the device. The combination of the device in accordance with the invention and the screw forms a fastening system, wherein the screw extends through the fixing element and the spring.

The fastening system in accordance with the invention has the advantage that the fastening device can be fitted onto the screw even before the screw is screwed in, i.e. before the patient is involved. In addition, forces which act on the fastening device and therefore on the patient when the adjusting screw is being operated are omitted. Furthermore, the spring automatically presses the fixing element against the bone due to its bias, without an adjusting screw having to be operated.

To this end, the fixing element is preferably arranged such that it can be shifted relative to the screw in the direction of the screw axis. The spring is arranged such that it presses the fixing element against the bone relative to the screw. This fixes the fixing element relative to the bone. The fixing element maintains the bias even when a screw or sleeve and the bone have settled, and therefore ensures that the rotational stability is guaranteed by a toothing constantly engaging with the bone. The device in accordance with the invention also has the advantage that the fixing element is automatically pressed deeper into the bone if the bone becomes softer over the course of time, such that even then, a good hold is guaranteed for the fastening device.

The fixing element is also preferably arranged such that it can be rotated relative to the screw about the screw axis. The fixing element can thus be fixed in the desired alignment independently of the rotational position of the screw relative to the bone.

It is particularly important that the fastening device is anchored in the bone in such a way that torque acting on the device does not alter the position of the device with respect to the bone. To this end, the screw according to the prior art is screwed bi-cortically into the bone. Bi-cortical screwing is also possible with the present fastening device, but not absolutely necessary.

In one embodiment of the invention, the side of the fixing element facing the bone comprises a supporting plate. Via the supporting plate, the fixing element lies on the bone over a large area, thus enabling unicortical screwing to be sufficient for absorbing torque acting on the device. The supporting plate is for example designed integrally with the fixing element or as a separate component which is fixedly connected to the fixing element, for example by being screwed on.

On the side of the fixing element facing the bone, the device preferably comprises at least one eccentrically arranged spike. If the spring exerts a force on the fixing element, the spike is pressed into the bone and so prevents the fixing element from rotating relative to the bone.

The abutment is for example a part of the screw, for example the head of a headed screw or a protrusion, i.e. a radial swelling of a Schanz screw. Alternatively, the fastening device comprises an abutment element comprising an abutment for the spring, wherein the spring is arranged such that it exerts a force between the abutment element and the fixing element which spreads the fastening device. The abutment element can be shifted in the direction of the screw axis relative to the fixing element. The abutment element is supported by the screw, for example by the head of a headed screw or a protrusion, i.e. a radial swelling, of a Schanz screw.

The abutment is advantageously designed to be adjustable. The fastening device can thus be adapted to the characteristics of the bone. On the one hand, a penetration depth of the screw which is dependent on the bone can be equalized, and on the other hand, the bias of the spring can be adapted to the hardness of the bone. The abutment consists for example of a screw nut on the abutment element or on the screw. The screw nut can be adjusted in the direction of the spring, i.e. along the screw axis. The screw nut can preferably be fixed relative to the abutment element and/or screw, for example by means of a clamping screw.

The spring is for example a helical spring. In one embodiment, the helical spring is fitted onto the screw such that the screw passes inside the helical spring in the axial direction. One end of the helical spring abuts the fixing element, the other end abuts an abutment on the screw. The screw and the helical spring and/or the fixing element are in particular arranged concentrically.

In another embodiment, the helical spring is fitted onto the abutment element, wherein the abutment element preferably extends through the spring, into the fixing element. The screw passes, preferably concentrically, through the abutment element, the helical spring and the fixing element. In this embodiment, the fixing element, the abutment element and the spring constitute an easy-to-handle unit which can be fixed to the bone in a single working step.

The fixing element is then for example designed to be sleeve-like, i.e. the fixing element comprises a hollow-cylindrical base part, and the screw extends into the inner region of said base part. The axis of the hollow cylinder is then substantially identical to or parallel to the axis of the screw. The mounting for the marker device is preferably situated at the end of the fixing element facing the spring, i.e. facing away from the bone. The extension of the fixing element in the axial direction thus results in a distance between the marker device and the bone which leaves space for the tissue surrounding the bone.

Alternatively, the fixing element is designed to be planar. This means that the extension of the fixing element in the axial direction of the screw is less than in a direction perpendicular to this and is for example at most 50%, 25%, 10% of 5% of this extension. The mounting for the marker device then advantageously consists of an arm on the fixing element.

Alternatively, the spring is a disc spring or leaf spring. Such a spring is in particular suitable if the fixing element exhibits a flat, for example disc-like basic shape. A fastening device comprising a headed screw, a flat fixing element and a disc spring or leaf spring is in particular suitable for being arranged between the bone and the tissue surrounding the bone. In this case, the mounting for the marker device is for example an arm which extends from the flat base part of the fixing element, through the tissue surrounding the bone.

In one embodiment of the invention, the device comprises a cutting device on the fixing element. The cutting device serves to enlarge, as required, the incision through which the fastening device enters the body. The incision is thus for example initially configured to be only large enough that through it, the fastening device can be anchored in the bone. If the tissue subsequently moves in relation to the bone, then the incision is enlarged by the cutting device just far enough that the fastening device can exit the body. Torque exerted on the fastening device in particular by the tissue is thus minimized.

The cutting device is preferably arranged such that it can be rotated relative to the fixing element, wherein the axis about which the cutting device can rotate relative to the fixing element corresponds in particular to the axis in which the fixing element can be rotated relative to the screw. Due to its rotatable arrangement, the cutting device can be automatically aligned in the cutting direction.

The cutting device is in particular one or more knives. The cutting edges of the knives extend for example in the axial direction of the screw.

BRIEF DESCRIPTION OF THE DRAWINGS

The present invention shall be illustrated in more detail on the basis of two example embodiments.

FIG. 6 shows the fastening device from FIG. 5, once it has been screwed on.

DETAILED DESCRIPTION

Figure 1:
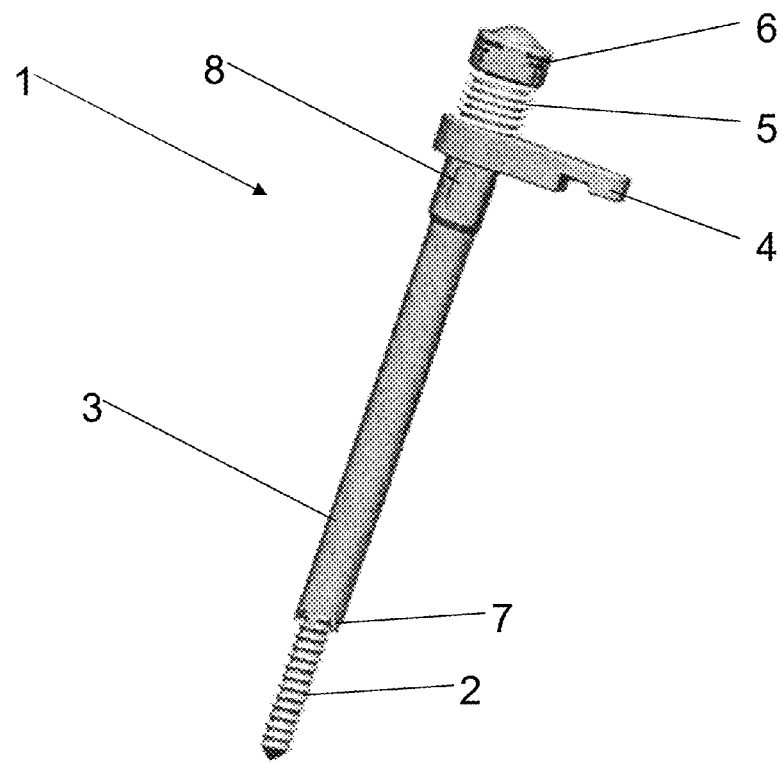
FIG. 1 shows a first design of the fastening device.

FIG. 1 shows a device 1 for fastening a marker device in a bone, in accordance with a first design. For the sake of clarity, both the marker device and the bone have been omitted in all the figures.

The device 1 comprises a fixing element 3 and a mounting 4 for the marker device on the fixing element 3. The fixing element 3 is embodied to be sleeve-like, i.e. it comprises a hollow-cylindrical base body. On one facing area of the hollow-cylindrical base body, the fixing element 3 comprises spikes 7 which penetrate into the bone when the device 1 is attached and prevent the fixing element 3 from rotating relative to the bone. A spring 5 abuts the opposite facing area of the fixing element 3 and also abuts an abutment. The abutment is formed by an area of an abutment element 6 which can be telescopically shifted relative to the fixing element 3 in the axial direction of the hollow-cylindrical base body, and one end of which enters the fixing element 3 through the spring 5.

When attaching the device 1, the fixing element 3 is placed onto the bone in the desired alignment, and the screw 2 is inserted through the device 1 and screwed into the bone, wherein the screw 2 passes through the fixing element 3, the spring 5 and the abutment element 6, for example concentrically. As of a certain penetration depth of the screw 2 into the bone, the abutment presses against the spring 5 and compresses it. This generates a spring force which causes the spikes 7 to penetrate into the bone and thus prevent the fixing element 3 from rotating relative to the bone and/or the screw 2.

The fixing element 3 can be shifted relative to the screw 2 in the direction of the screw axis. The fixing element 3 can also be rotated about the screw 2, wherein the rotational axis substantially corresponds to the screw axis of the screw 2. To this end, the hollow-cylindrical base body of the fixing element 3 exhibits an inner diameter which is slightly larger than the outer diameter of the thread of the screw 2. The part of the screw 2 which passes through the fixing element 3 is optionally unthreaded.

The abutment element 6 abuts the head of the screw 2 in order to transfer the force applied by the spring onto the screw 2. Alternatively, the head of the screw 2 directly serves as the abutment for the spring 5, i.e. in this case, an abutment element 6 is not provided. A cleaning opening 8 at the end of the fixing element 3 facing the spring serves for cleaning the device 1.

Figure 2:
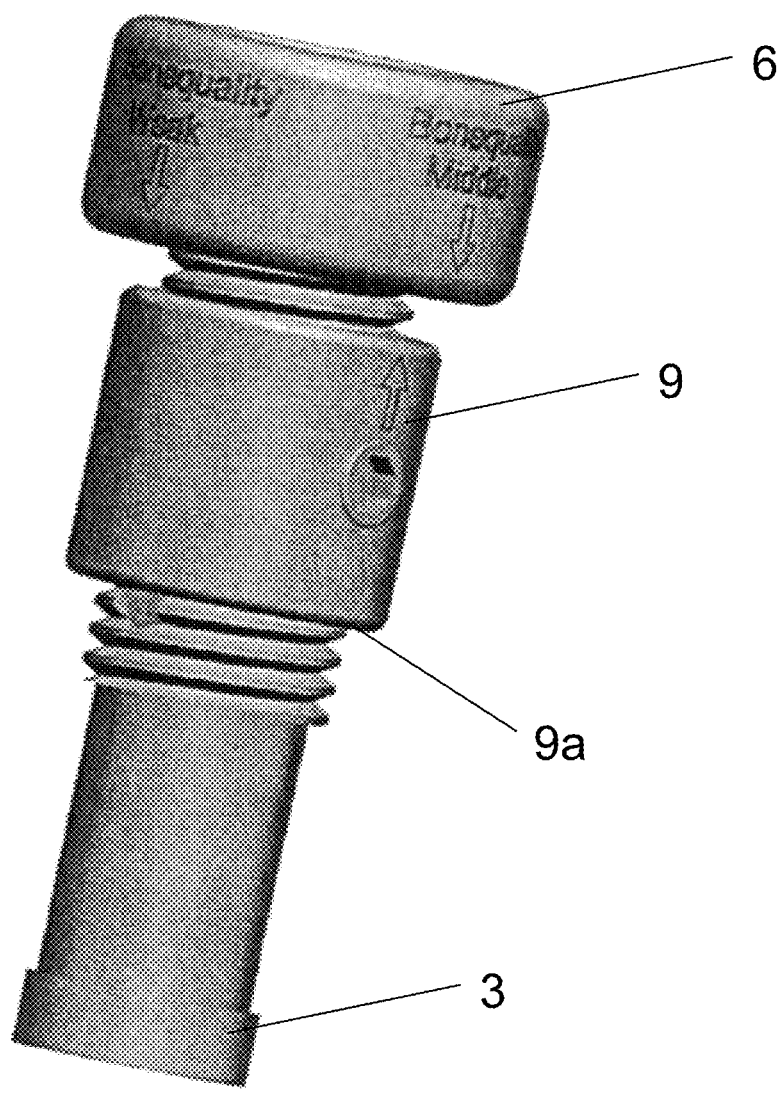
FIG. 2 shows an adjustable spring abutment.

FIG. 2 shows an optional mechanism for an adjustable abutment. In this case, the head of the abutment element 6 does not serve directly as the abutment for the spring 5 but rather the area 9*a* of a screw nut 9 which is screwed onto the abutment element 6. Rotating the screw nut 9 shifts it in the axial direction of the screw 2 relative to the abutment element 6 and thus relative to the head of the screw 2. This results in a change in the penetration depth of the screw 2 into the bone as of which the spring 5 begins to be biased. The device 1 can thus be adapted to the characteristics of the bone, by adjusting the penetration depth of the screw 2 into the bone at which the spring 5 exhibits the desired bias. Another result is that the spring force is adapted to the hardness of the bone. The screw nut 9 is alternatively situated directly on the screw 2, if a separate abutment element 6 is not provided.

Figure 3:
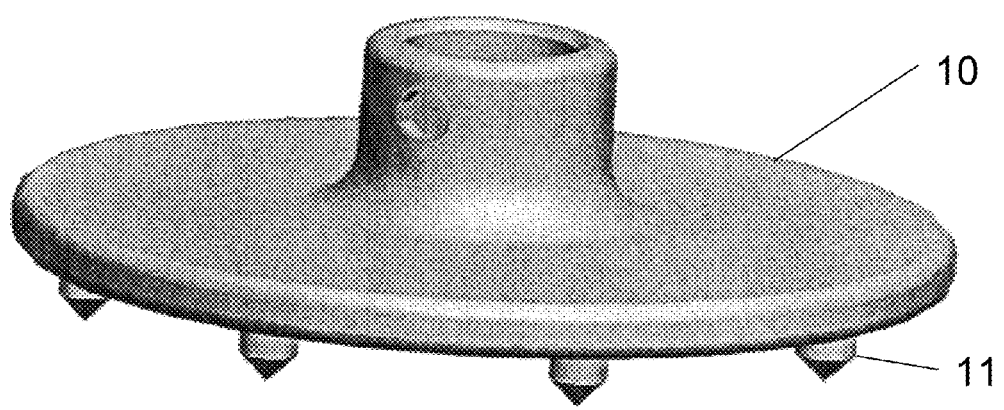
FIG. 3 shows a supporting plate.

FIG. 3 shows a supporting plate 10 which is fitted onto the fixing element 3 and screwed to it. The supporting plate 10 serves to support the device 1 on the bone over a large area, in order that torque acting on the device 1 does not cause the device to tilt relative to the bone. To this end, the supporting plate 10 is fitted precisely far enough onto the fixing element 3 that the spikes 7 on the side of the fixing element 3 facing the bone still protrude beyond the supporting plate 10. The supporting plate 10 comprises additional spikes 11 which, like the spikes 7, prevent the fixing element 3 from rotating relative to the bone. It is optionally possible to design the supporting plate 10 integrally with the fixing element 3.

Figure 4:
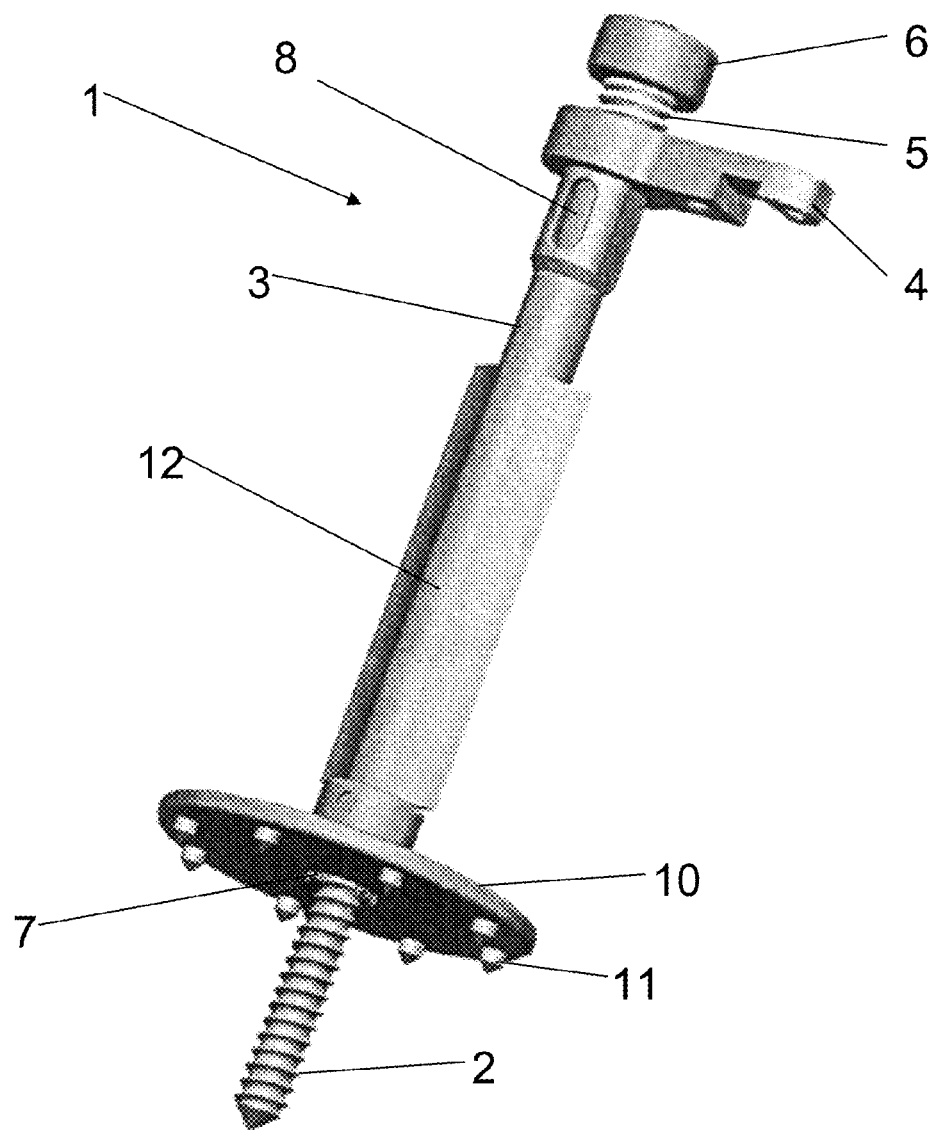
FIG. 4 shows the fastening device from FIG. 1, with additional equipment features.

FIG. 4 shows the device 1 together with the additional supporting plate 10 and a cutting device 12. The cutting device 12 surrounds the fixing element 3 and comprises two blades which extend in the axial direction of the hollow-cylindrical base part of the fixing element 3, i.e. the screw 2. The two cutting edges are situated on diametrically opposite sides of the cutting device 12. The cutting device 12 can be rotated relative to the fixing element 3 about the longitudinal axis of the fixing element 3. It serves to broaden, if required, the incision through which the device 1 is placed onto the bone and screwed to it, wherein the tissue surrounding the bone is cut open just far enough that no force or only a small force is exerted on the device 1.

Figure 5:
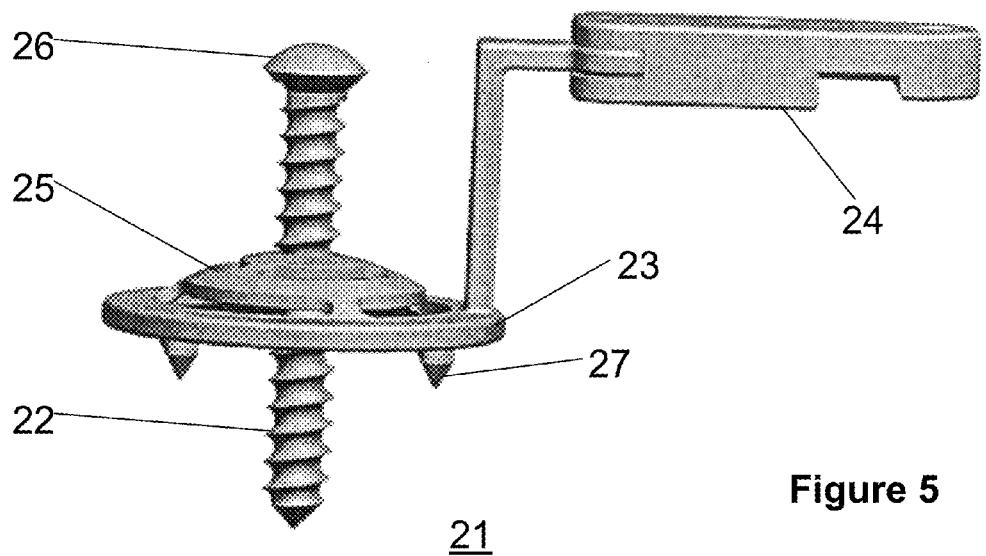
FIG. 5 shows a second design of the fastening device, before it has been attached.
Figure 6:
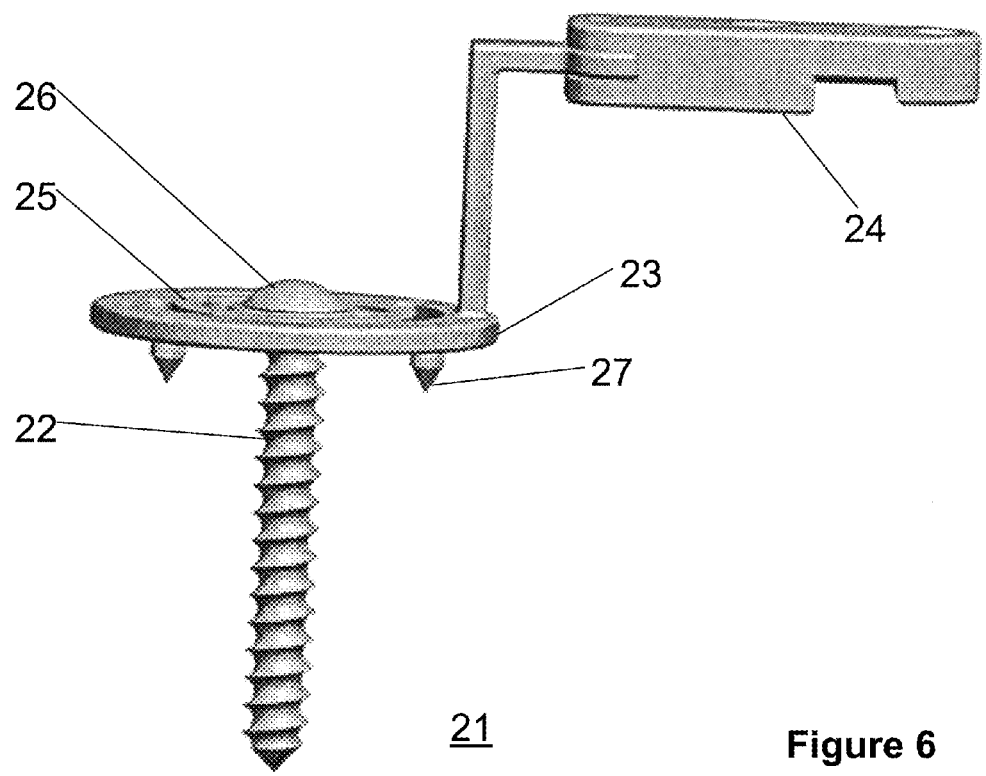

FIGS. 5 and 6 show a device 21 for fastening a marker device to a bone in accordance with a second design, comprising a fixing element 23 and a disc spring 25, wherein the fixing element 23, as opposed to the fixing element 3, is designed to be planar instead of sleeve-like. An arm, serving as the mounting 24 for the marker device, extends from the planar—in the present example embodiment, circular disc-shaped—base body of the fixing element 23. A screw 22 serves to fix the device 21 in the bone.

The screw 22 penetrates through each of the disc spring 25 and the circular disc-shaped base part of the fixing element 23 in their centre points. The disc spring 25 is arranged between the fixing element 23 and the head 26 of the screw 22. The head 26 of the screw 22 serves as the abutment for the disc spring 25. Spikes 27 are arranged on the side of the fixing element 23 opposite the disc spring 25 and penetrate into the bone and prevent the fixing element 23 from rotating relative to the bone. The fixing element 23 can be rotated about a screw 22 and shifted relative to the screw 22 in the direction of the screw axis.

FIG. 5 shows the device 21 before it has been attached to the bone. When attaching the device 21, the fixing element 23 is placed onto the bone and aligned relative to the bone. The screw 22 is then rotated through the device 21 and into the bone. As of a certain penetration depth of the screw 22 into the bone, the head 26 of the screw 22 abuts the disc spring 25 and compresses it. As of this point in time, the disc spring 25 generates a force onto the fixing element 23 which presses the spikes 27 into the bone. If the screw 22 is rotated further into the bone, the disc spring 25 is increasingly biased.

The end state, in which the screw 22 has been screwed completely into the bone, is shown in FIG. 6. If the bone becomes soft due to the force applied by the spikes 27, the disc spring 25 is relaxed and presses the spikes 27 deeper into the bone. This ensures that the fixing element 23 is fixed relative to the bone, without the screw 22 having to be readjusted. Optionally, more than one screw is provided for fixing the device in the bone, wherein a spring is preferably provided for each screw.

It is possible to combine individual features of the example embodiments with each other. It is thus for example possible to provide the device 21 with an adjustable abutment or to use a disc spring instead of a helical spring in the device 1.

Computer program elements of the invention may be embodied in hardware and/or software (including firmware, resident software, micro-code, etc.). The computer program elements of the invention may take the form of a computer program product which may be embodied by a computer-usable or computer-readable storage medium comprising computer-usable or computer-readable program instructions, "code" or a "computer program" embodied in said medium for use by or in connection with the instruction executing system. Within the context of this application, a computer-usable or computer-readable medium may be any medium which can contain, store, communicate, propagate or transport the program for use by or in connection with the instruction executing system, apparatus or device. The computer-usable or computer-readable medium may for example be, but is not limited to, an electronic, magnetic, optical, electro-magnetic, infrared or semiconductor system, apparatus, device or medium of propagation, such as for example the Internet. The computer-usable or computer-readable medium could even for example be paper or another suitable medium on which the program is printed, since the program could be electronically captured, for example by optically scanning the paper or other suitable medium, and then compiled, interpreted or otherwise processed in a suitable manner. The computer program product and any software and/or hardware described here form the various means for performing the functions of the invention in the example embodiment(s).

Although the invention has been shown and described with respect to one or more particular preferred embodiments, it is clear that equivalent amendments or modifications will occur to the person skilled in the art when reading and interpreting the text and enclosed drawing(s) of this specification. In particular with regard to the various functions performed by the elements (components, assemblies, devices, compositions, etc.) described above, the terms used to describe such elements (including any reference to a "means") are intended, unless expressly indicated otherwise, to correspond to any element which performs the specified function of the element described, i.e. which is functionally equivalent to it, even if it is not structurally equivalent to the disclosed structure which performs the function in the example embodiment(s) illustrated here. Moreover, while a particular feature of the invention may have been described above with respect to only one or some of the embodiments illustrated, such a feature may also be combined with one or more other features of the other embodiments, in any way such as may be desirable or advantageous for any given application of the invention.

What is claimed is:

1. A device for fastening a marker device to a bone, comprising:
   a screw having a threaded distal end for screwing into the bone and thereby securing the screw to the bone;
   a fixing element having a distal side for contacting the bone, wherein an extent of the fixing element in an axial direction of the screw is less than in a direction perpendicular to the screw, the fixing element having a through passage for receiving the screw and the fixing element including a mount spaced apart from the distal side and laterally offset from the through passage, the mount configured to fixedly attach the marker device to the fixing element; and
   a resilient member interposed between a proximal side of the fixing element and an abutment on a portion of the screw that is more proximal than the fixing element for resiliently biasing the fixing element into forced engagement with the bone to inhibit rotation of the fixing element relative to the bone;

wherein the abutment on the screw is adjustably movable relative to the screw in an axial direction of the screw.

2. The device according to claim 1, comprising at least one spike on a side of the fixing element for facing the bone.

3. The device according to claim 1, wherein the abutment comprises a threaded nut configured to compress the resilient member.

4. The device according to claim 1, wherein the resilient member comprises a helical spring, a disc spring or a leaf spring.

5. The device according to claim 1, comprising a cutting device on the fixing element.

6. The device according to claim 5, wherein the cutting device is rotatable relative to the fixing element.

7. The device according to claim 5, wherein the cutting device comprises a blade.

8. The device according to claim 1, wherein the fixing element is movable relative to the screw in the direction of the screw axis.

9. The device according to claim 1, wherein the fixing element is rotatable relative to the screw about the screw axis.

10. The device according to claim 1, wherein the mount comprises an arm extending radially out from the fixing element.

11. The device according to claim 1, wherein the distal side of the fixing element comprises spikes, wherein when the fixing element contacts the bone the spikes prevent rotation of the fixing element relative to the bone.

12. The device according to claim 1, wherein the mount is arranged between the distal side and the abutment.

13. The device according to claim 1, wherein the fixing element is movable relative to the screw in the direction along an axis of the screw.

* * * * *